(12) United States Patent
Terada et al.

(10) Patent No.: US 8,582,202 B2
(45) Date of Patent: Nov. 12, 2013

(54) OBSERVING DEVICE AND METHOD

(75) Inventors: Hirotoshi Terada, Hamamatsu (JP); Hiroshi Tanabe, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 653 days.

(21) Appl. No.: 12/665,588

(22) PCT Filed: Jun. 13, 2008

(86) PCT No.: PCT/JP2008/060893
§ 371 (c)(1),
(2), (4) Date: Feb. 22, 2010

(87) PCT Pub. No.: WO2008/156038
PCT Pub. Date: Dec. 24, 2008

(65) Prior Publication Data
US 2010/0202041 A1 Aug. 12, 2010

(30) Foreign Application Priority Data
Jun. 20, 2007 (JP) ................................ P2007-163188

(51) Int. Cl.
*G02B 21/00* (2006.01)
(52) U.S. Cl.
USPC ............................ 359/368; 359/819; 359/811
(58) Field of Classification Search
USPC ................. 359/368–384, 665, 811, 819–830; 355/53
See application file for complete search history.

(56) References Cited

U.S. PATENT DOCUMENTS

| 5,939,709 | A | * | 8/1999 | Ghislain et al. | ............... 250/216 |
| 6,785,204 | B1 | | 8/2004 | Okuyama et al. | |
| 6,828,811 | B2 | * | 12/2004 | Hanson et al. | ............. 356/237.5 |
| 7,042,647 | B2 | * | 5/2006 | Lo | ................................. 359/652 |
| 7,123,035 | B2 | * | 10/2006 | Hanson et al. | ............. 356/237.1 |
| 7,414,800 | B2 | * | 8/2008 | Isobe et al. | ..................... 359/811 |

(Continued)

FOREIGN PATENT DOCUMENTS

| EP | 1 041 545 | 10/2000 |
| EP | 1 667 131 | 6/2006 |

(Continued)

OTHER PUBLICATIONS

Notice of Allowance dated Sep. 9, 2011 that issued in U.S. Appl. No. 12/664,105.

*Primary Examiner* — Stephone Allen
*Assistant Examiner* — James McGee
(74) *Attorney, Agent, or Firm* — Drinker Biddle & Reath LLP

(57) ABSTRACT

When it is detected that a solid immersion lens comes into contact with the semiconductor device, the lens is caused to vibrate by a vibration generator unit. Next, a reflected light image from the lens is input to calculate a reflected light quantity of the reflected light image, and it is judged whether a ratio of the reflected light quantity to an incident light quantity is not greater than a threshold value. When the ratio is greater than the threshold value, it is judged that optical close contact between the lens and the semiconductor device is not achieved, and the lens is again caused to vibrate. When the ratio is not greater than the threshold value, it is judged that optical close contact between the lens and the semiconductor device is achieved, and an observed image of the semiconductor device is acquired.

9 Claims, 14 Drawing Sheets

(56) References Cited

U.S. PATENT DOCUMENTS

| | | |
|---|---|---|
| 7,576,910 B2 * | 8/2009 | Terada et al. ............... 359/383 |
| 7,576,928 B2 * | 8/2009 | Tanabe et al. ............... 359/819 |
| 7,639,025 B2 | 12/2009 | Hanson et al. |
| 2001/0021145 A1 * | 9/2001 | Ichimura et al. ............. 369/43 |
| 2005/0027288 A1 * | 2/2005 | Oyagi et al. ................. 606/16 |
| 2005/0094293 A1 * | 5/2005 | Tanabe et al. ............... 359/811 |
| 2006/0182001 A1 | 8/2006 | Isobe et al. |
| 2010/0172035 A1 | 7/2010 | Terada et al. |
| 2010/0202041 A1 | 8/2010 | Terada et al. |

FOREIGN PATENT DOCUMENTS

| | | |
|---|---|---|
| JP | 5-328961 | 12/1993 |
| JP | 2003107358 A * | 4/2003 |
| JP | 2006-201404 | 8/2006 |
| JP | 2006-201407 | 8/2006 |
| WO | WO 2004-083929 | 9/2004 |
| WO | WO 2005/043210 | 5/2005 |

* cited by examiner

Fig.5
(a)
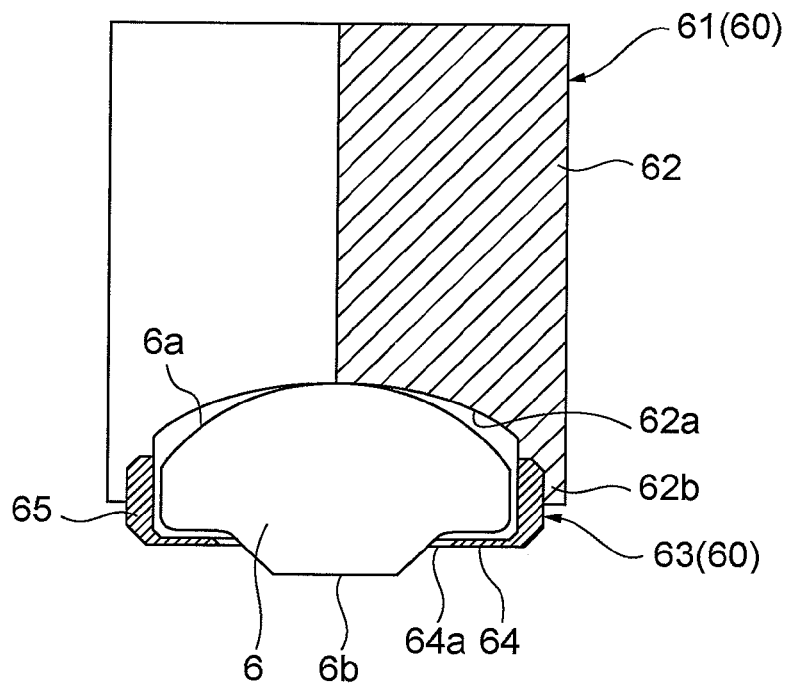
(b)
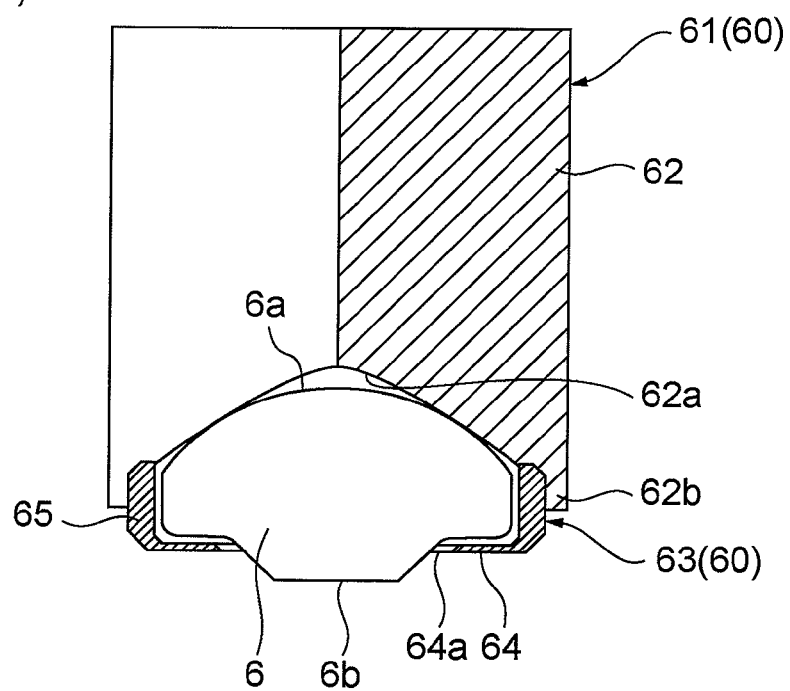

Fig.9
(a)
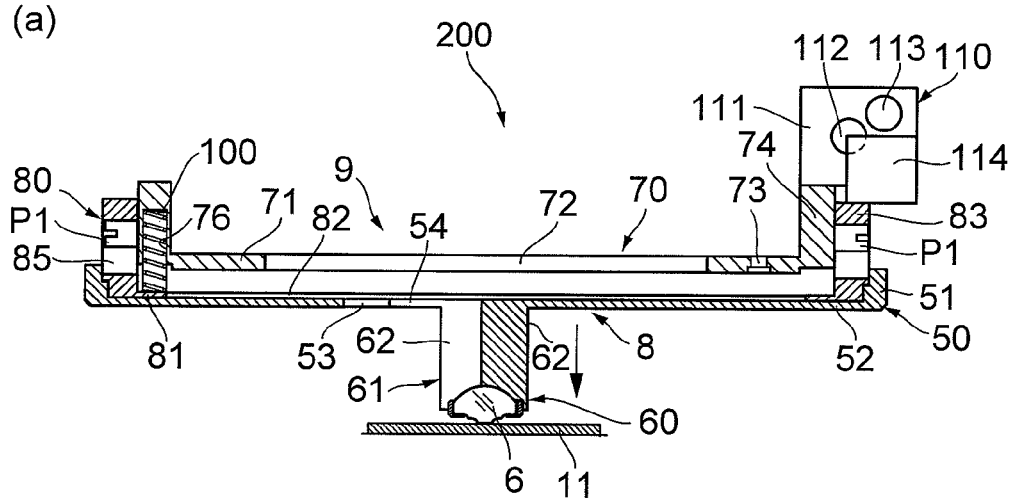
(b)
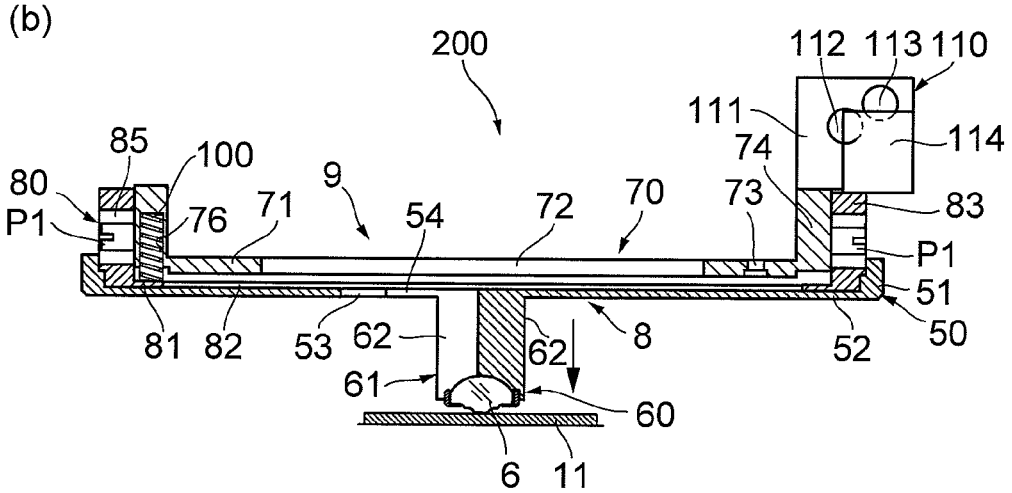
(c)
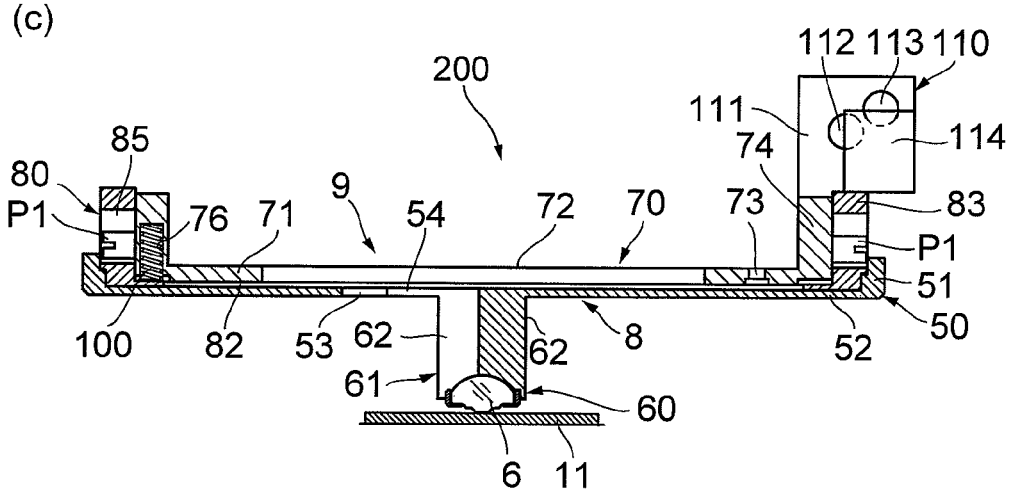

OBSERVING DEVICE AND METHOD

TECHNICAL FIELD

The present invention relates to an observation apparatus and method for observing an observation object by utilizing a solid immersion lens.

BACKGROUND ART

As a lens that magnifies an image of an observation object, a solid immersion lens (SIL: Solid Immersion Lens) is known. A solid immersion lens has a hemispherical shape or a hyperhemispherical shape called Weierstrass sphere, that is a microlens of about 1 mm to 5 mm in size. Then, provided that the solid immersion lens is installed so as to be made to contact closely with the surface of an observation object, its numerical aperture (NA) and magnification are both magnified, which enables an observation with high spatial resolution.

As an observation apparatus utilizing a solid immersion lens, for example, an apparatus disclosed in Patent Document 1 is known. The observation apparatus disclosed in Patent Document 1 includes a microscope having an objective lens, and a solid immersion lens holder which is coupled to a front end of the objective lens via an arm member, that holds a solid immersion lens on the front surface side of the objective lens.
Patent Document 1: International Publication No. 2005/043210 Pamphlet

DISCLOSURE OF THE INVENTION

Problems to be Solved by the Invention

Meanwhile, when observing an observation object by utilizing a solid immersion lens as in the above-described conventional art, unless the solid immersion lens and the observation object are made to favorably contact closely with one another, it is difficult to achieve optical coupling (evanescent coupling) between the solid immersion lens and the observation object.

An object of the present invention is to provide an observation apparatus and method which are capable of improving the close contact property between a solid immersion lens and an observation object.

Means for Solving the Problems

An observation apparatus of the present invention includes a microscope having an optical system including an objective lens, that magnifies an observation object to observe it, a solid immersion lens holder that holds a solid immersion lens disposed on an optical axis of the objective lens, and vibration generating means for causing the solid immersion lens held by the solid immersion lens holder to vibrate.

In the case in which an observation object is observed by use of the observation apparatus of the present invention, the solid immersion lens held by the solid immersion lens holder is caused to contact closely with the observation object, and the observation object is observed in that state with the microscope. At this time, depending on a fabrication state of a lens holding surface of the solid immersion lens holder or the observation object for example, in some cases, it is impossible to achieve favorable close contact between the solid immersion lens and the observation object. In this case, when the solid immersion lens held by the solid immersion lens holder is caused to vibrate by the vibration generating means, the solid immersion lens is caused to adhere tightly along the surface of the observation object. Thereby, it is possible to achieve favorable close contact between the solid immersion lens and the observation object.

An observation method of the present invention includes a step of preparing an observation apparatus which includes a microscope having an optical system including an objective lens, that magnifies an observation object to observe it, a solid immersion lens holder that holds a solid immersion lens disposed on an optical axis of the objective lens, and vibration generating means for causing the solid immersion lens held by the solid immersion lens holder to vibrate, a step of causing the solid immersion lens held by the solid immersion lens holder to vibrate by the vibration generating means, to cause the solid immersion lens to contact closely with the observation object, and a step of observing the observation object with the microscope after the solid immersion lens is caused to contact closely with the observation object.

In this way, provided that the solid immersion lens held by the solid immersion lens holder is caused to vibrate, to cause the solid immersion lens to contact closely with the observation object, the solid immersion lens is caused to adhere tightly along the surface of the observation object regardless of a fabrication state of the lens holding surface of the solid immersion lens holder or the observation object for example. Thereby, it is possible to achieve favorable close contact between the solid immersion lens and the observation object.

Effect of the Invention

In accordance with the present invention, it is possible to improve the close contact between a solid immersion lens and an observation object. Thereby, it is possible to achieve appropriate optical coupling (evanescent coupling) between the solid immersion lens and the observation object.

BRIEF DESCRIPTION OF THE DRAWINGS

FIG. 5 shows enlarged sectional views showing a state in which the solid immersion lens shown in FIG. 4 is held by a lens holding unit.

FIG. 9 shows cross sectional views showing operations of the member position detecting unit and the solid immersion lens holder shown in FIG. 8.

DESCRIPTION OF THE SYMBOLS

1—Semiconductor inspecting apparatus (observation apparatus), 3—High-sensitivity camera (image acquiring means), 4—LSM unit (illuminating means, contact detecting means, image acquiring means), 5—Microscope, 6—Solid immersion lens, 8—Holder main body, 11—Semiconductor device (observation object), 20—Optical system, 21—Objective lens, 32—LSM controller (contact detecting means, image acquiring means), 33—Peripheral controller (vibration control means), 41—Image analyzing unit, 41a—Image input unit (image acquiring means), 41c—Luminance value calculating unit (analysis means), 41d—Incident light quantity acquiring unit (analysis means), 41e—Threshold value storage unit (analysis means), 41f—Optical coupling judging unit (analysis means), 42—Instruction unit (vibration control means, contact detecting means), 60—Lens holding unit (vibration generating means), 110—Member position detecting unit (contact detecting means), 120—Vibration generator unit (vibration generating means), 200—Solid immersion lens holder.

BEST MODES FOR CARRYING OUT THE INVENTION

Hereinafter, a preferred embodiment of the observation apparatus and method according to the present invention will be described with reference to the drawings. Note that, the same components in the respective drawings are denoted by the same reference symbols, and overlapping descriptions will be omitted.

Figure 1:
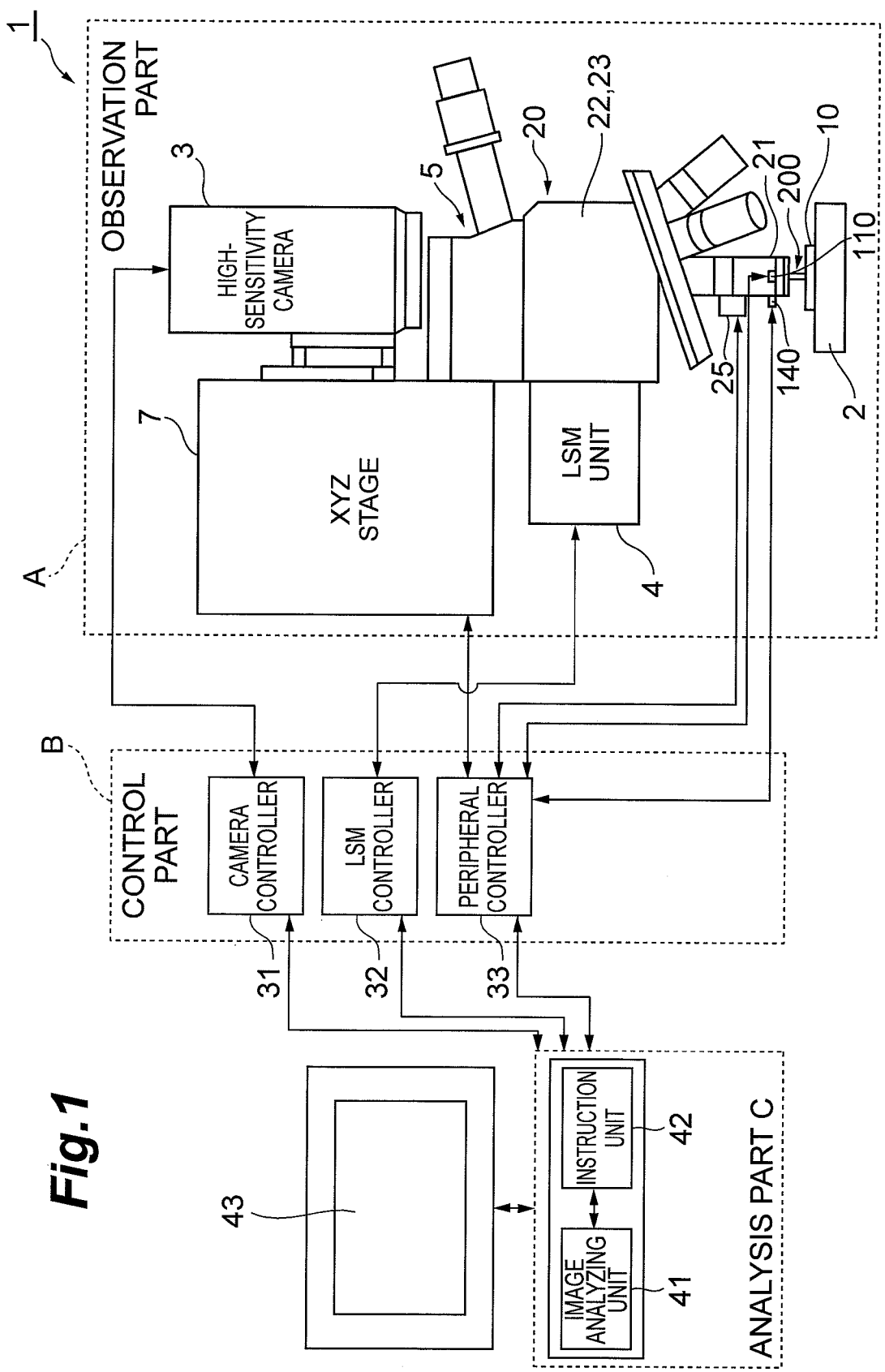
FIG. 1 is a block diagram of a semiconductor inspecting apparatus, that is an embodiment of an observation apparatus according to the present invention.
Figure 2:
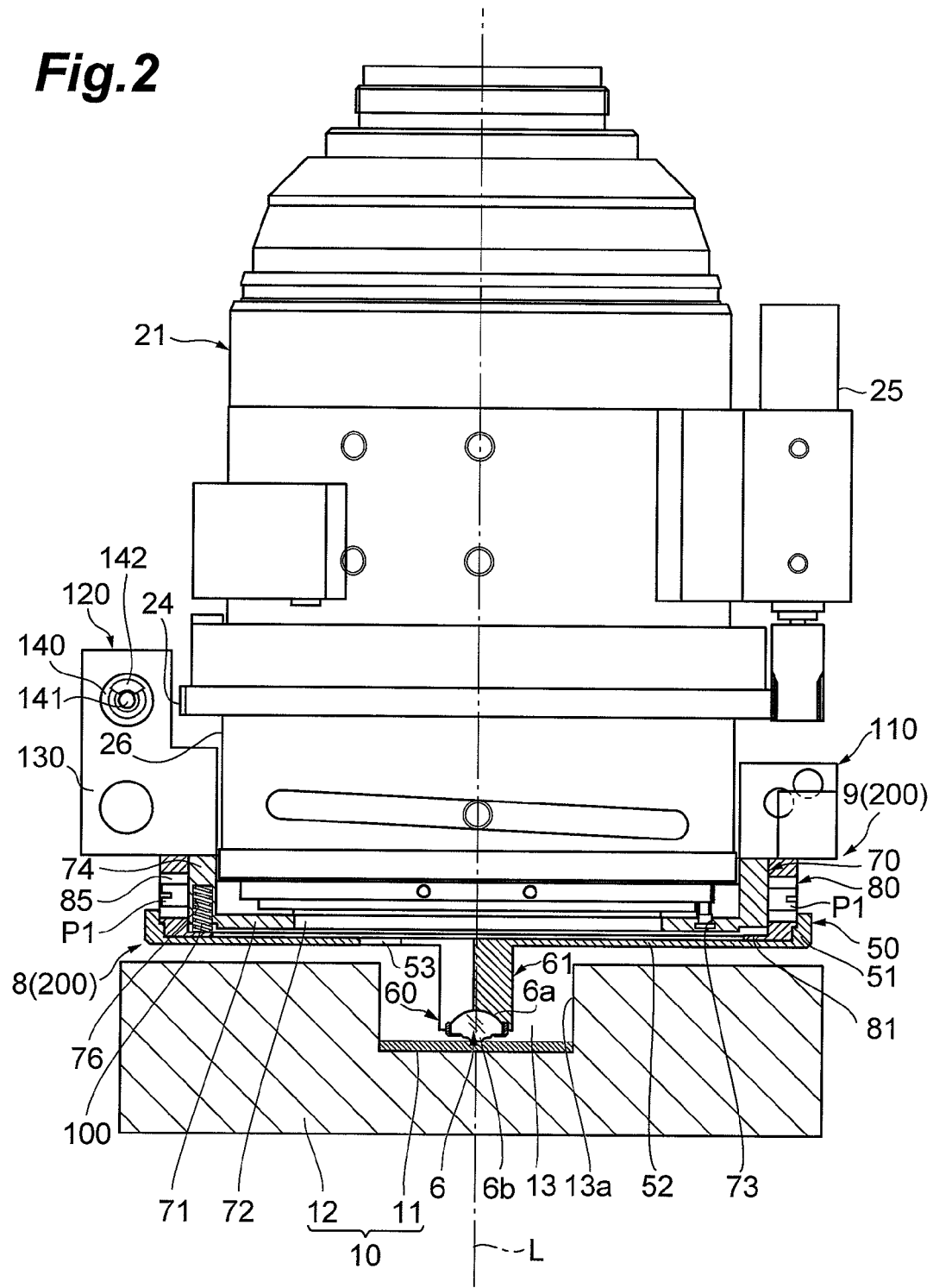
FIG. 2 is a cross sectional view showing a configuration of an objective lens and the solid immersion lens holder in a microscope shown in FIG. 1.
Figure 3:
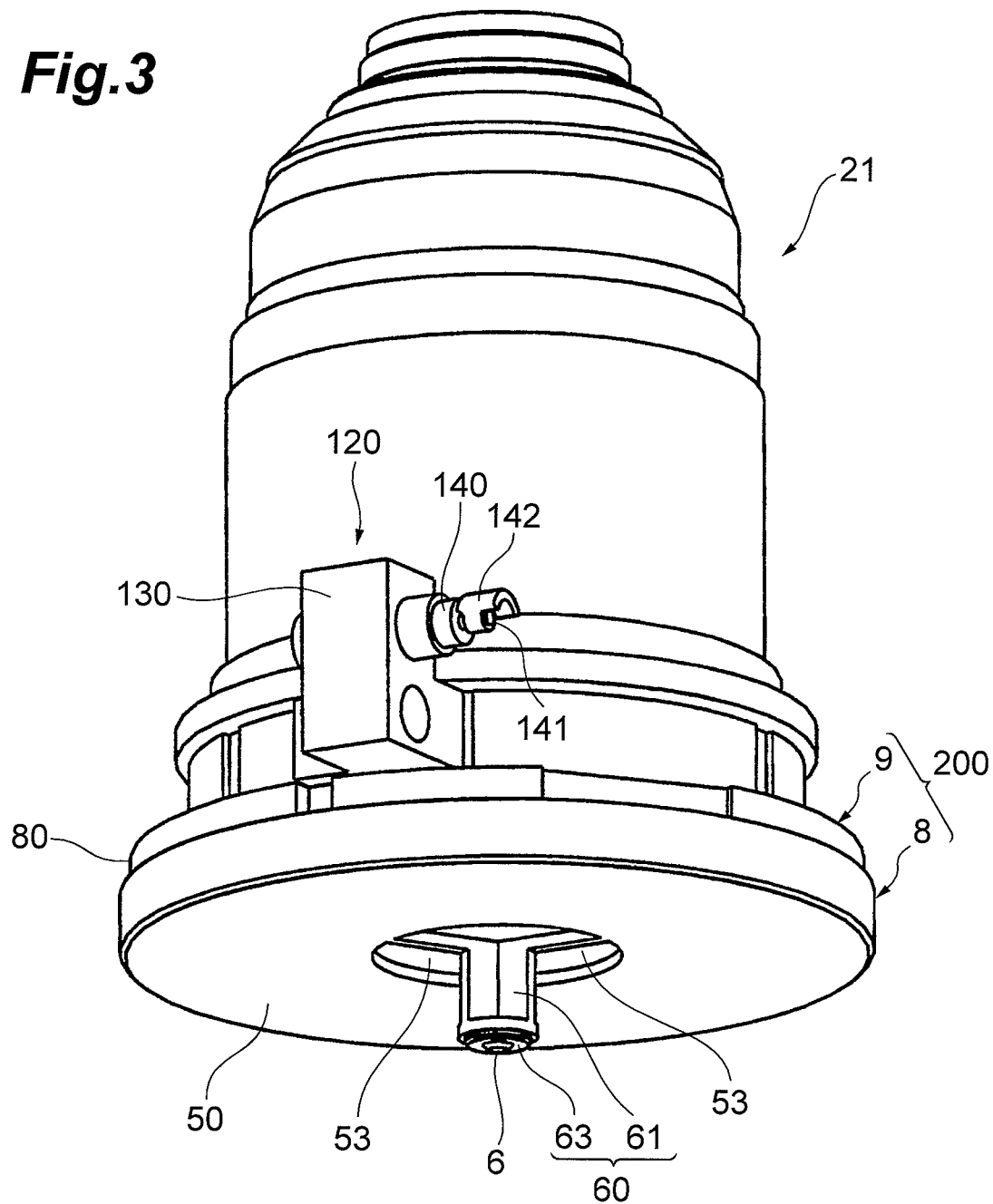
FIG. 3 is a perspective view of the objective lens and the solid immersion lens holder shown in FIG. 2.

FIG. 1 is a block diagram of a semiconductor inspecting apparatus, that is an embodiment of an observation apparatus according to the present invention. FIG. 2 is a cross sectional view showing a configuration of an objective lens and a solid immersion lens holder in a microscope, that is one of the main parts of the semiconductor inspecting apparatus shown in FIG. 1, and FIG. 3 is a perspective view of the objective lens and the solid immersion lens holder shown in FIG. 2. Here, FIG. 2 shows a state in an observation of a sample. The following descriptions will be given such that the objective lens side is set as an upper side and the sample side is set as a lower side with respect to a solid immersion lens.

As shown in FIGS. 1 and 2, a semiconductor inspecting apparatus 1 is an inspecting apparatus that, for example, uses a semiconductor device 11, that is provided in a mold-type semiconductor device serving as a sample 10, as an observation object, and acquires an image of the semiconductor device 11 to inspect the internal information thereof.

The term "mold-type semiconductor device" means that the semiconductor device 11 is molded with resin 12. Further, the term "internal information" includes a circuit pattern of the semiconductor device and very weak emission from the semiconductor device. As such very weak emission, emission caused by an abnormal place based on a defect in the semiconductor device, transient emission according to a switching operation of a transistor in the semiconductor device, and the like are cited. Moreover, heat generation based on a defect in the semiconductor device as well is included.

The sample 10 is placed on a stage 2 provided in an observation part A such that the rear surface of the semiconductor device 11 turns up in a state in which the resin 12 is cut such that the rear surface of the semiconductor device 11 buried in the resin 12 is exposed. Because the rear surface of the semiconductor device 11 is exposed by cutting a part of the sample 10 in this way, the semiconductor device 11 is to be located on the bottom surface of a depressed portion 13 formed by cutting the resin 12. Then, the inspecting apparatus 1 inspects the lower surface in the drawing of the semiconductor device 11 (an integrated circuit and the like formed on the front surface of the substrate of the semiconductor device 11) in the present embodiment.

The semiconductor inspecting apparatus 1 includes the observation part A for performing an observation of the semiconductor device 11, a control part B for controlling the operations of the respective units in the observation part A, and an analysis part C for executing processing, an instruction, and the like necessary for an inspection for the semiconductor device 11.

The observation part A is equipped with a high-sensitivity camera 3 and a laser scanning optical system (LSM: Laser Scanning Microscope) unit 4 serving as image acquiring means for acquiring an image from the semiconductor device 11, a microscope 5 which is disposed between the high-sensitivity camera 3, the LSM unit 4 and the semiconductor device 11, and which has an optical system 20 including an objective lens 21, a solid immersion lens 6 (refer to FIG. 2) for acquiring a magnified observed image of the semiconductor device 11, and an XYZ stage 7 that respectively moves those in the X-Y-Z directions perpendicular to each other.

The optical system 20 includes an optical system for camera 22 and an optical system for LSM unit 23 in addition to the above-described objective lens 21. A plurality of the objective lenses 21 different in magnifications are provided to be switchable. Further, the objective lens 21 has a correction ring 24, and the objective lens 21 is capable of performing an aberration correction in an observation by adjusting the correction ring 24. The optical system for camera 22 guides a light from the semiconductor device 11 through the objective lens 21 to the high-sensitivity camera 3. Thereby, the high-sensitivity camera 3 acquires an image of the circuit pattern and the like of the semiconductor device 11.

On the other hand, the optical system for LSM unit 23 reflects an infrared laser light from the LSM unit 4 to the objective lens 21 side with a beam splitter (not shown) to guide the infrared laser light to the semiconductor device 11, and guides the laser light reflected from the semiconductor device 11 heading to the high-sensitivity camera 3 through the objective lens 21, to the LSM unit 4.

The LSM unit 4 forms illuminating means for causing an infrared laser light to scan in the X-Y direction to radiate it to the semiconductor device 11 side, and in addition, the LSM unit detects a reflected light from the semiconductor device 11 with a photodetector (not shown). The intensity of the detected light is an intensity in which the circuit pattern of the semiconductor device 11 is reflected. Accordingly, the LSM unit 4 acquires an image of the circuit pattern and the like of the semiconductor device 11 due to an infrared laser light scanning the semiconductor device 11 in the X-Y direction.

Further, the XYZ stage 7 is to move the high-sensitivity camera 3, the LSM unit 4, the microscope 5, the solid immersion lens 6, and the like respectively in the X-Y direction (the horizontal direction; a direction parallel to the semiconductor device 11 serving as an observation object) and the Z direction (the vertical direction) perpendicular to the X-Y direction as needed.

The control part B includes a camera controller 31, a laser scanning (LSM) controller 32, and a peripheral controller 33. The camera controller 31 and the LSM controller 32 respectively control the operations of the high-sensitivity camera 3 and the LSM unit 4, to control the execution of an observation (image acquisition), the setting for observation conditions, and the like for the semiconductor device 11, which are performed in the observation part A.

The peripheral controller 33 controls the operation of the XYZ stage 7 to control movements, alignments, focusing, and the like of the high-sensitivity camera 3, the LSM unit 4, the optical system 20, and the like to a position corresponding to an observation position for the semiconductor device 11. At this time, the peripheral controller 33 controls the operation of the XYZ stage 7 in accordance with detection results from various sensors and the like attached to a solid immersion lens holder 200. Further, the peripheral controller 33 drives a correction ring adjusting motor 25 attached to the objective lens 21 to adjust the correction ring 24.

Moreover, the peripheral controller 33 controls driving of a vibrating motor 140 attached to the solid immersion lens holder 200.

The solid immersion lens holder 200 including the vibrating motor 140 will be described in detail later.

The analysis part C includes an image analyzing unit 41 and an instruction unit 42, and is composed of a computer. The image analyzing unit 41 executes analysis processing and the like necessary for image information from the camera controller 31 and the LSM controller 32. The instruction unit 42 performs a necessary instruction on the execution of an inspection for the semiconductor device 11 in the observation part A via the control part B with reference to an input content from an operator, an analyzed content by the image analyzing unit 41, or the like. Further, an image, data, or the like acquired or analyzed by the analysis part C is displayed on a display device 43 connected to the analysis part C as needed.

As shown in FIG. 2, the solid immersion lens 6 is a hemispherical minute lens, that has a top surface 6a formed into a spherical shape, which serves as an input/output surface for light with respect to the outside (for example, the objective lens 21 of the microscope 5), and a bottom surface 6b formed into a planar shape, which serves as an attaching surface for the semiconductor device 11. Provided that the bottom surface 6b of the solid immersion lens 6 contacts closely with an observation position (the top surface in the drawing) of the semiconductor device 11, it is possible to acquire a magnified observed image of the surface of the semiconductor device 11 (the lower surface in the drawing) that is the reverse side thereof.

In detail, the solid immersion lens 6 is composed of a material having a high refractive index that is substantially the same or approximate to the refractive index of the substrate material of the semiconductor device 11. Si, GaP, GaAs, and the like can be cited as representative examples thereof. The minute solid immersion lens 6 is made to optically contact closely with the surface of the substrate of the semiconductor device 11, to utilize the semiconductor substrate itself as a part of the solid immersion lens 6. In accordance with the rear surface analysis of the semiconductor device 11 by utilizing the solid immersion lens 6, a light flux with high NA is allowed to pass through the substrate by the effect of the solid immersion lens 6 when the objective lens 21 is focused on the integrated circuit formed on the front surface of the semiconductor substrate, which results in a potentially high-resolution.

The lens shape of the solid immersion lens 6 is determined under the condition for eliminating aberration. In the solid immersion lens 6 having a hemispherical shape, the center of the sphere is to be the focal point. At this time, its numerical aperture (NA) and magnification are both n-fold. In addition, the shape of the solid immersion lens 6 is not limited to having a hemispherical shape, and may have a Weierstrass shape for example.

The solid immersion lens holder 200 is to appropriately hold the solid immersion lens 6 with respect to the objective lens 21. The solid immersion lens holder 200 includes a holder main body 8 and an objective lens socket 9 for attaching the holder main body 8 to the front end of the objective lens 21.

Figure 4:
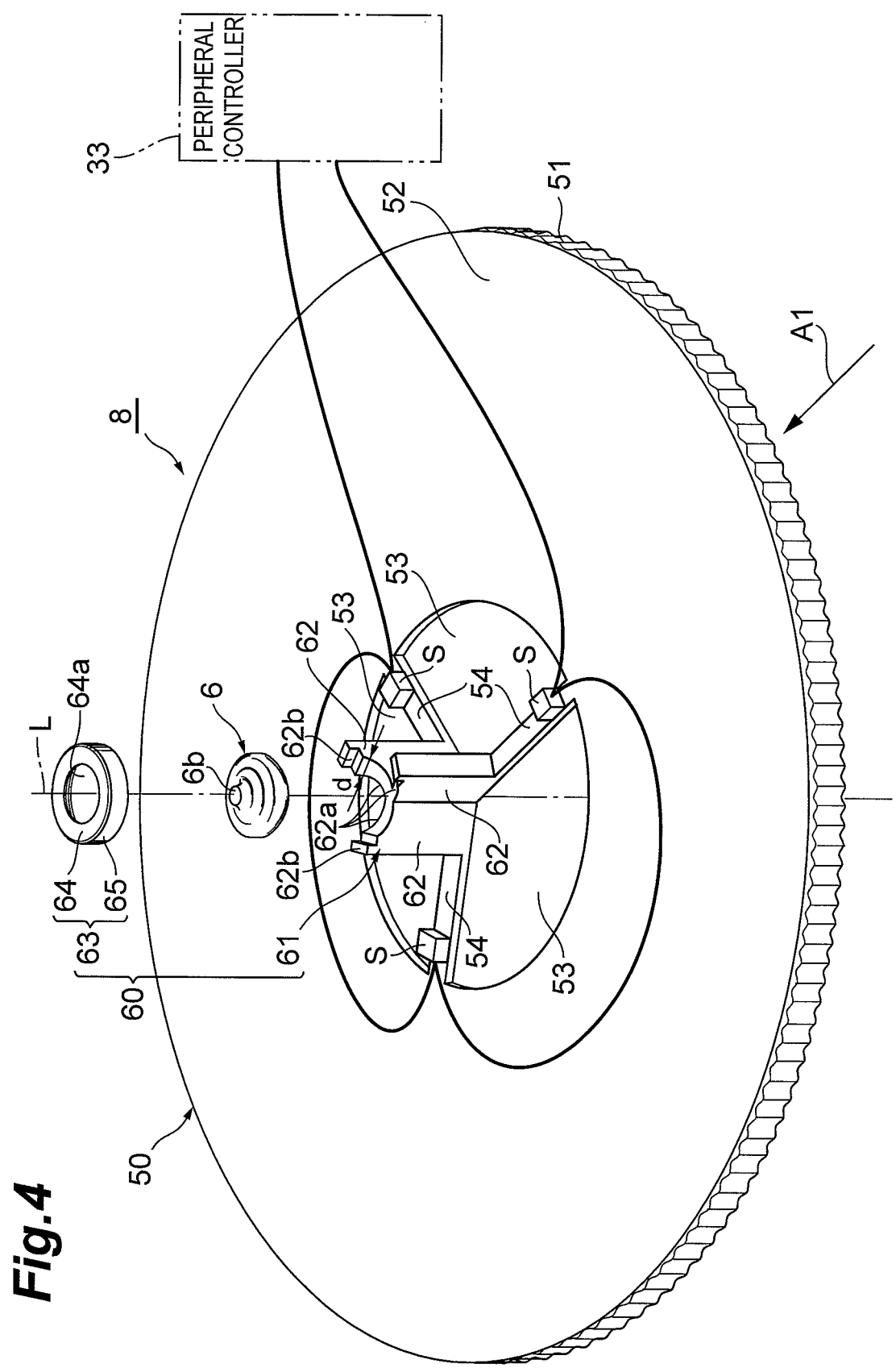
FIG. 4 is an exploded perspective view of a holder main body shown in FIG. 2.

FIG. 4 is an exploded perspective view of the holder main body 8. As shown in FIGS. 2 to 4, the holder main body 8 has a discoid objective lens cap 50 and a lens holding unit 60 extending in a direction approximately perpendicular to the objective lens cap 50 from the center of the objective lens cap 50. When viewed from the direction of arrow A1 shown in FIG. 4, the outer shape of the holder main body 8 is an approximately T-shape.

The objective lens cap 50 has a peripheral wall 51 screwed together to the objective lens socket 9 (refer to FIG. 2), and is attached to the leading end of the objective lens 21 via the objective lens socket 9. A bottom plate 52 forming the objective lens cap 50 has three openings 53 for allowing light flux to pass through. The respective openings 53 allow light output from the LSM unit 4 to pass through to the solid immersion lens 6 side, and allow the light which is reflected by the semiconductor device 11 and output from the solid immersion lens 6, to pass through to the objective lens 21 side. The respective openings 53 are formed into approximately sector shapes, and are disposed respectively concentrically to the center of the objective lens cap 50, and at equal intervals in the circumferential direction. Thereby, three connecting parts 54 for connecting the lens holding unit 60 and the bottom plate 52, which extend in a radial pattern from the center of the objective lens cap 50 are formed at equal intervals between the adjacent openings 53 and 53.

The lens holding unit 60 has a lens holding member 61 extending in a direction approximately perpendicular to the objective lens cap 50 (in the optical axis L direction of the objective lens 21) from the intersecting portion of the three connecting parts 54, and a cylindrical lens cover 63. The lens holding member 61 is composed of three holding pieces 62 located on the respective connecting parts 54 and to receive the solid immersion lens 6. The respective holding pieces 62 are disposed in a radial pattern with respect to the center line of the lens holding member 61, and have a tapered shape whose width d becomes narrower as it goes to the center line of the lens holding member 61.

Lens receiving surfaces 62a having a curvature approximately the same as a curvature of the top surface 6a of the solid immersion lens 6 are respectively formed on the leading ends of the respective holding pieces 62 (the ends opposite to the objective lens cap 50), and the lens holding member 61 receives the solid immersion lens 6 stably with the three lens receiving surfaces 62a. Further, claw parts 62b for fixing the lens cover 63 are respectively formed on the leading ends of the respective holding pieces 62. The lens cover 63 has a bottom plate 64, and a peripheral wall 65 to be fit into the claw parts 62b is provided at the peripheral portion of the bottom plate 64. An opening 64a for allowing the bottom surface 6b of the solid immersion lens 6 to project to the outside (the sample 10 side) is formed in the bottom plate 64.

FIG. 5 shows enlarged sectional views showing a state in which the solid immersion lens 6 is held by the lens holding unit 60. In this configuration, when the solid immersion lens 6 is disposed between the lens receiving surfaces 62a of the lens holding member 61 and the lens cover 63, and the lens cover 63 is fixed to the lens holding member 61 with an adhesive or the like, the solid immersion lens 6 is housed and held between the lens receiving surfaces 62a and the lens cover 63 in a state in which the bottom surface 6b of the solid immersion lens 6 projects from the opening 64a.

In a state in which the solid immersion lens 6 is held by the lens holding unit 60, a gap (clearance) is provided between the top surface 6a of the solid immersion lens 6 and the lens receiving surfaces 62a of the lens holding member 61. Therefore, the solid immersion lens 6 is held in a state of being unfixed to be free with respect to the lens holding unit 60. Thereby, the solid immersion lens 6 is allowed to freely move with respect to the lens holding member 61.

In a state in which the solid immersion lens 6 is out of contact with the semiconductor device 11, the solid immersion lens 6 is supported in its own weight direction by the bottom plate 64 of the lens cover 63. On the other hand, in a state in which the solid immersion lens 6 is in contact with the semiconductor device 11 by moving the objective lens 21 in the optical axis L direction by an operation of the XYZ stage 7, the solid immersion lens 6 is supported in a state in which the top surface 6a of the solid immersion lens 6 is in contact with the lens receiving surfaces 62a of the lens holding member 61, and the solid immersion lens 6 is separated from the bottom plate 64 of the lens cover 63. At this time, because the solid immersion lens 6 is held in a state of being free with respect to the lens holding member 61, when the solid immersion lens 6 comes into contact with the semiconductor device 11, the bottom surface 6b of the solid immersion lens 6 easily adheres tightly along the rear surface of the semiconductor device 11.

The solid immersion lens holder is preferably structured such that the tip of the top surface 6a of the solid immersion lens 6 comes into single point contact with the lens receiving surfaces 62a of the lens holding member 61 as shown in (a) in FIG. 5 in a state in which the solid immersion lens 6 and the semiconductor device 11 are in contact with each other. Thereby, because the solid immersion lens 6 is allowed to move fully with respect to the lens holding member 61 centering on the contact point, it is possible to achieve favorable surface contact between the solid immersion lens 6 and the semiconductor device 11.

However, because the lens receiving surfaces 62a have a curved shape (an R shape), it is extremely difficult to improve the fabrication accuracy of the lens receiving surfaces 62a, and it is unavoidable to generate a fabrication error in curvature radius of the lens receiving surfaces 62a. Therefore, in a state in which the solid immersion lens 6 and the semiconductor device 11 are in contact with each other, as shown in (b) in FIG. 5, plural portions of the top surface 6a of the solid immersion lens 6 may come into contact with the lens receiving surfaces 62a of the lens holding member 61 in some cases.

When the solid immersion lens 6 is further pushed down for adjusting a focus position or the like in a state in which the solid immersion lens 6 is in contact with the semiconductor device 11, the semiconductor device 11 could be damaged by force applied from the solid immersion lens 6. Then, it is preferable that the holder main body 8 respectively has detection stress detecting sensors S that detect stress applied to the respective connecting parts 54 as shown in FIG. 4. The respective stress detecting sensors S are electrically connected to the peripheral controller 33, and when force greater than or equal to a predetermined stress is detected by the stress detecting sensors S, the peripheral controller 33 stops driving of the XYZ stage 7. Thereby, force greater than or equal to a predetermined load is not applied to the semiconductor device 11.

Figure 6:
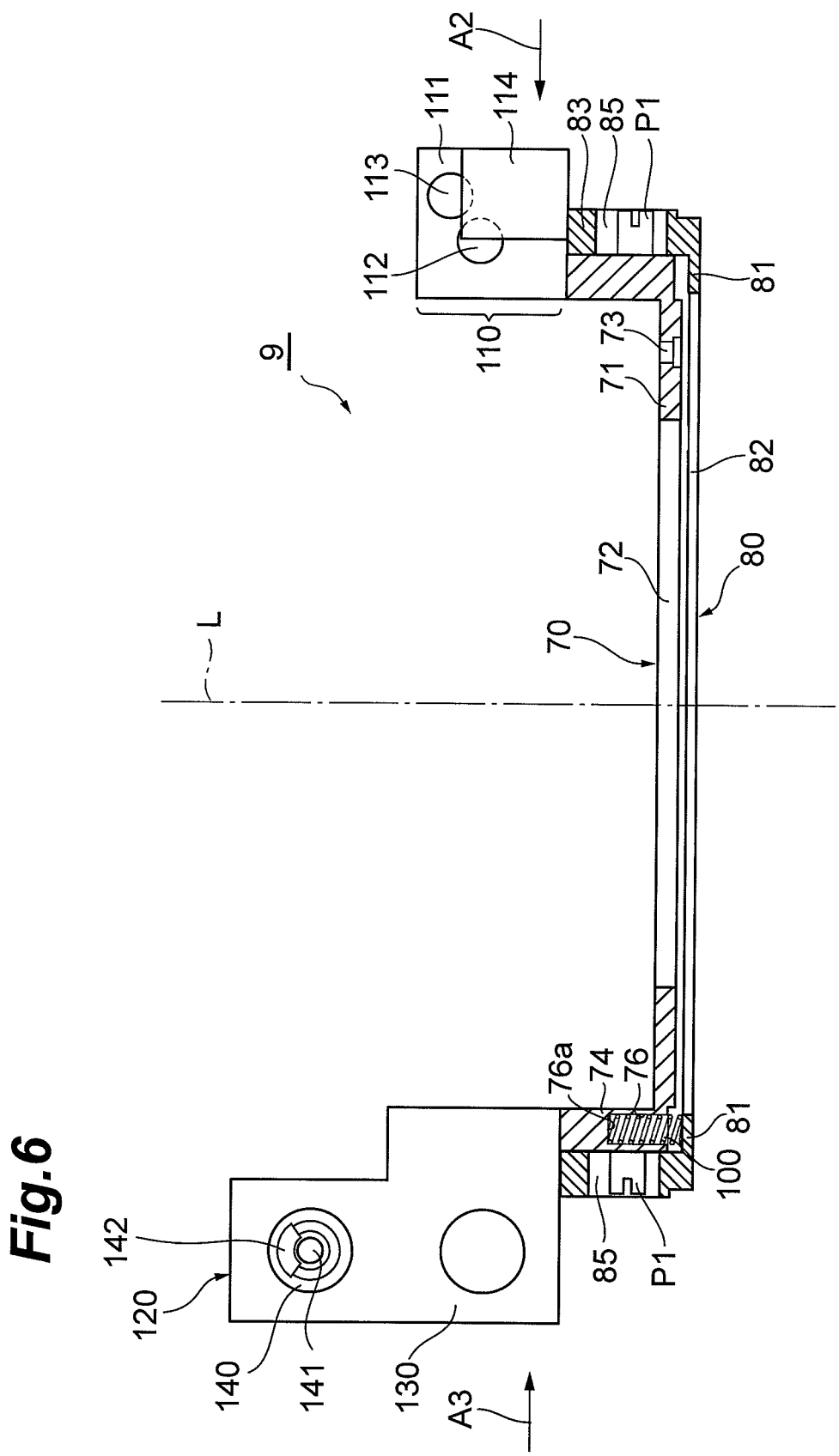
FIG. 6 is a cross sectional view of an objective lens socket shown in FIG. 2.

FIG. 6 is a cross sectional view of the objective lens socket 9. As shown in FIGS. 2 and 6, the objective lens socket 9 has a cylindrical base part 70 fit into the leading end (front end) of an objective lens body tube 26 of the objective lens 21, and a movable member 80 fit into the base part 70.

Figure 7:
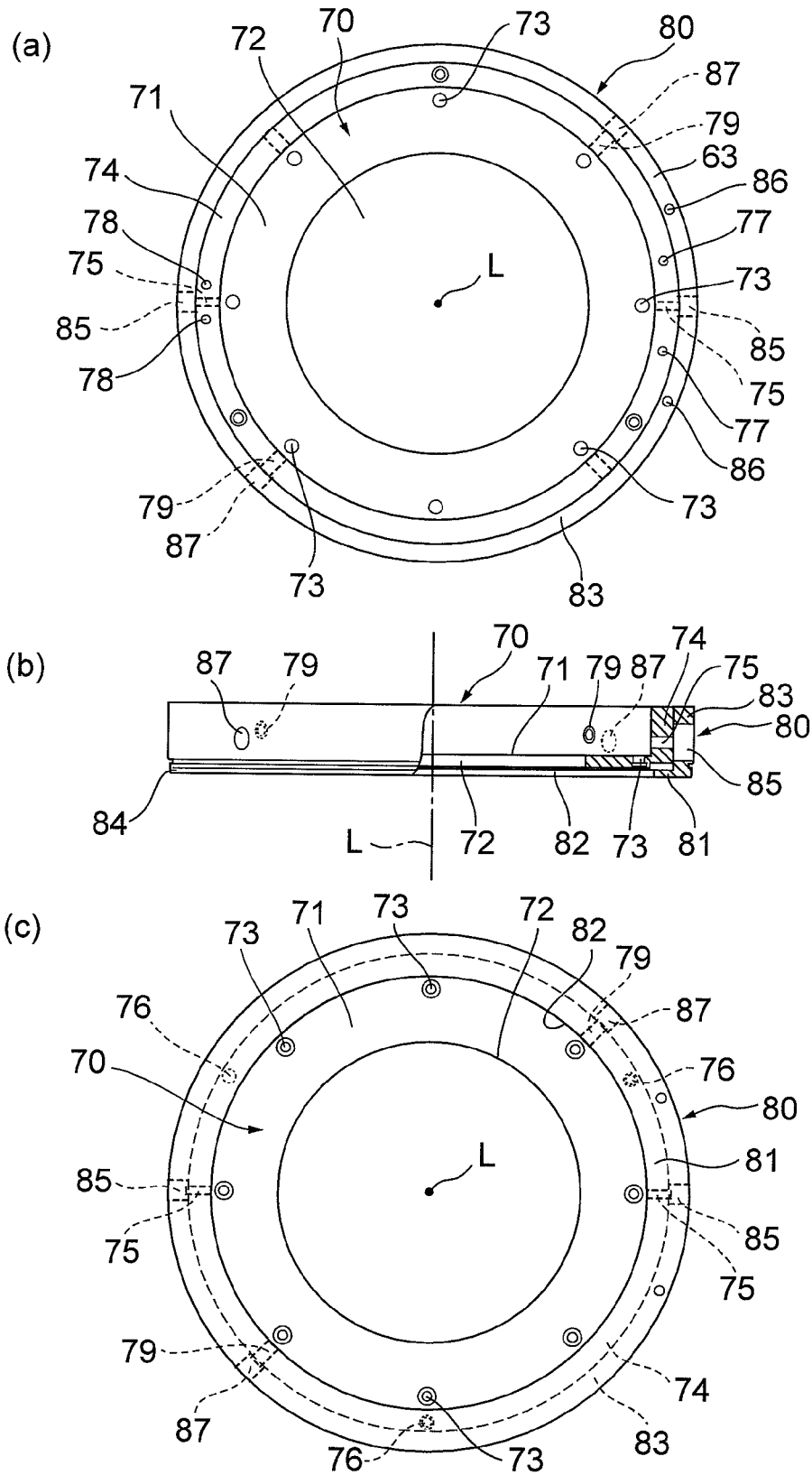
FIG. 7 shows a plan view, a side view (including a partial cross sectional view), and a rear surface view of the objective lens socket shown in FIG. 6.

(a) in FIG. 7 is a diagram of the base part 70 and the movable member 80 viewed from the objective lens 21 side, (b) in FIG. 7 is a side view of the base part 70 and the movable member 80, and (c) in FIG. 7 is a diagram of the base part 70 and the movable member 80 viewed from the sample 10 side. FIG. 7 shows the state in which the movable member 80 is fit into the base part 70, however, illustrations of connecting pins and the like are omitted.

As shown in FIGS. 6 and 7, the base part 70 and the movable member 80 respectively have bottom plates 71 and 81, and circular openings 72 and 82 for allowing a light flux output from the objective lens 21 or a light flux made to come into the objective lens 21 to pass through are respectively formed on the central side of the bottom plates 71 and 81. It suffices to set diameters of the openings 72 and 82 in size so as not to block a light flux, and the diameter of the opening 82 is made greater than the diameter of the opening 72. A plurality of through holes 73 are formed around the opening 72 of the base part 70, and the base part 70 is screwed to the objective lens body tube 26 of the objective lens 21 via the through holes 73.

Peripheral walls 74 and 83 are respectively provided at the peripheral portions of the bottom plates 71 and 81. The inner diameter of the peripheral wall 74 is equal to the outer diameter of the leading end of the objective lens body tube 26, and the base part 70 is fit into the leading end of the objective lens body tube 26 of the objective lens 21 to be attached.

Further, the outer diameter of the peripheral wall 74 is equal to the inner diameter of the peripheral wall 83, and the movable member 80 is to be fit into the base part 70. Then, the outer surface of the peripheral wall 74 and the inner surface of the peripheral wall 83 are in contact with each other so as to slide, and as a result thereof, the movable member 80 is slidable in the optical axis L direction with respect to the base part 70. The outer diameter of the peripheral wall 83 (the outer diameter of the movable member 80) is equal to the inner diameter of the peripheral wall 51 of the objective lens cap 50 (refer to FIG. 2). Then, a thread groove 84 (refer to FIG. 7(b)) for allowing the peripheral wall 51 of the objective lens cap 50 to be screwed together thereto is formed on the outer circumferential surface of the end on the bottom plate 81 side of the movable member 80, which allows the objective lens cap 50 to be attached to the movable member 80.

A pair of through holes 85 facing each other are provided in the peripheral wall 83 of the movable member 80, and the movable member 80 is coupled to the base part 70 by inserting pins P1 into through holes 75 formed at positions respectively corresponding to the respective through holes 85 in the peripheral wall 74 of the base part 70. The through hole 85 has an oval shape whose length in the optical axis L direction is longer than its circumferential length, and the circumferential length of the through hole 85 is approximately the same as the outer diameter of the pin P1. As a result, the movable member 80 is movable in the optical axis L direction with respect to the base part 70 by the length in the optical axis L direction of the oval shape, and is prevented from rotating circumferentially.

The base part 70 and the movable member 80 are fit into one another so as to interpose springs 100 respectively housed in three spring housing grooves 76 formed in the bottom surface of the peripheral wall 74 of the base part 70. Here, FIG. 2 shows the spring housing groove 76 and the through hole 85 in the same section, however, the layout relationship therebetween is different in reality, and the actual layout is shown in FIG. 7. Because the depth of the spring housing groove 76 is shorter than the natural length of the spring 100, the leading end of the spring 100 projects from the spring housing groove 76.

Accordingly, in a state in which the movable member 80 is fit into the base part 70, the both ends of the spring 100 respectively touch a bottom surface 76a of the spring housing groove 76 (the upper surface in FIG. 6) and the bottom plate 81 of the movable member 80, to bias the movable member 80 in the optical axis L direction. Thereby, the solid immersion lens 6 is biased to contact closely with the semiconductor device 11 when observing the semiconductor device 11.

Here, if the biasing force by the spring 100 is too strong, the semiconductor device 11 could be damaged as described above. Therefore, the objective lens socket 9 has a member position detecting unit 110 that detects a position in the optical axis L direction of the movable member 80 (a member position) with respect to the base part 70, as shown in FIGS. 2 and 6.

Figure 8:
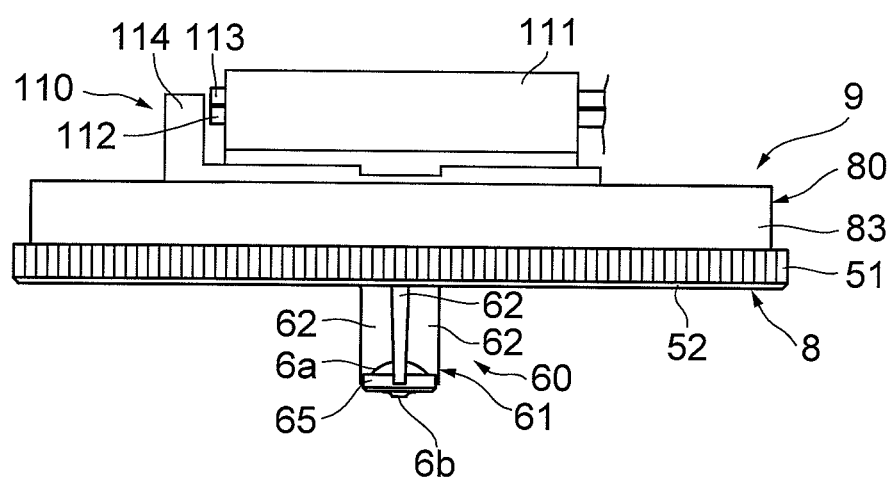
FIG. 8 is a diagram of a member position detecting unit shown in FIG. 6.

FIG. 8 is a diagram showing a configuration of the member position detecting unit 110. FIG. 8 shows a state of the unit viewed from the direction of arrow A2 in FIG. 6, that is a diagram in a state in which the holder main body 8 is attached. As shown in FIGS. 6 and 8, the member position detecting unit 110 has a sensor holding member 111, two proximity sensors 112 and 113 held by the sensor holding member 111, and an approximately L-shaped metal plate 114.

The sensor holding member 111 is an approximately rectangular parallelepiped in outer shape, that is screwed to thread holes 77 (refer to FIG. 7(a)) formed in the top surface of the peripheral wall 74 of the base part 70. The sensor holding member 111 holds the proximity sensors 112 and 113 such that the leading ends of the proximity sensors 112 and 113 project from the sensor holding member 111.

The metal plate 114 is screwed to thread holes 86 (refer to FIG. 7(a)) formed in the top surface of the peripheral wall 83 of the movable member 80, and moves in the optical axis L direction in accordance with the movable member 80. Then, the metal plate 114 is disposed so as to make its part (a portion extending in the optical axis L direction) face the proximity sensors 112 and 113.

The proximity sensors 112 and 113 are held by the sensor holding member 111 in a state of being disposed at different levels in the optical axis L direction, and in parallel in a direction perpendicular to the optical axis L direction. The proximity sensors 112 and 113 are electrically connected to the peripheral controller 33 (refer to FIG. 1), and detect a position of the movable member 80 with respect to the base part 70 by detecting the metal plate 114 on the basis of a change in magnetic field due to the metal plate 114 approaching (moving upward in FIG. 6).

The proximity sensor 112 is disposed so as to face the metal plate 114 when the springs 100 disposed between the base part 70 and the movable member 80 start shrinking from the natural length. Thereby, when the solid immersion lens 6 comes into contact with the semiconductor device 11, the proximity sensor 112 detects the metal plate 114. Therefore, the proximity sensor 112 functions as a sensor that detects a position of the movable member 80 corresponding to a contact starting position between the solid immersion lens 6 and the semiconductor device 11.

Further, the proximity sensor 113 is disposed above the proximity sensor 112, and detects a position of the movable member 80 for stopping bias against the semiconductor device 11 by the springs 100 via the solid immersion lens 6. That is, the proximity sensor 113 is disposed at a position above the proximity sensor 112 in order to detect a position of the movable member 80 with respect to the base part 70 at which maximum biasing force to the extent of not damaging the semiconductor device 11 is produced.

Here, the operations of the member position detecting unit 110 will be described with reference to FIG. 9. As shown in (a) in FIG. 9, first, when the objective lens socket 9 is pushed down with the objective lens 21 to the semiconductor device 11 side while carrying out an adjustment of a focus position of the objective lens 21 by the peripheral controller 33, the solid immersion lens 6 comes into contact with the semiconductor device 11.

Because the solid immersion lens 6 is held by the holder main body 8 attached to the movable member 80, when the solid immersion lens 6 comes into contact with the semiconductor device 11, the movable member 80 is pushed to the base part 70 side, and as a result, because the metal plate 114 as well moves upward, the proximity sensor 112 detects the metal plate 114. That is, the contact of the solid immersion lens 6 with the semiconductor device 11 is detected. The detection result by the proximity sensor 112 is input to the instruction unit 42 via the peripheral controller 33, to inform an operator (an observer) that the solid immersion lens 6 has come into contact with the semiconductor device 11.

Then, as shown in (b) in FIG. 9, in a state in which the objective lens 21 is further pushed down to the semiconductor device 11 side (that is, a state in which the objective lens socket 9 is pushed down), the proximity sensor 112 continues to output the detection result denoting that the metal plate 114 is detected, and in a state in which the proximity sensor 113 does not detect the metal plate 114, an adjustment of a focus position is continuously carried out.

Further, as shown in (c) in FIG. 9, when the objective lens socket 9 is further pushed down to the semiconductor device 11 side, and the proximity sensor 113 detects the metal plate 114, the peripheral controller 33 stops to push down the objective lens 21. Thereby, because a load greater than or equal to the set biasing force is not applied to the semiconductor device 11, the semiconductor device 11 is inhibited from being damaged by an adjustment of a focus position or the like.

Meanwhile, as described above, depending on a fabrication state of the lens receiving surfaces 62a of the lens holding member 61 in the holder main body 8, when the solid immersion lens 6 comes into contact with the semiconductor device 11, plural places on the solid immersion lens 6 come into contact with the lens receiving surfaces 62a as shown in (b) in FIG. 5 in some cases, and in this case, it is difficult for the solid immersion lens 6 to move. Further, even in the case in which the top surface 6a of the solid immersion lens 6 is in a state of single point contact with the lens receiving surfaces 62a as shown in (a) in FIG. 5 when the solid immersion lens 6 comes into contact with the semiconductor device 11, the solid immersion lens 6 may be inhibited from freely moving due to burrs, dust, or the like generated on the lens receiving surfaces 62a, for example. In such a case, the close contact between the solid immersion lens 6 and the semiconductor device 11 could be insufficient.

Then, the semiconductor inspecting apparatus 1 of the present embodiment further includes a vibration generator unit 120 that causes the holder main body 8 of the solid immersion lens holder 200 to vibrate as shown in FIGS. 2, 3, and 6 in order to securely cause the solid immersion lens 6 to contact closely with the semiconductor device 11.

The vibration generator unit 120 has an approximately L-shaped motor holding member 130 and the vibrating motor 140 (described above) held by and fixed to the motor holding member 130. The vibrating motor 140 is electrically connected to the peripheral controller 33 (refer to FIG. 1).

The motor holding member 130 is screwed to the thread holes 77 (refer to FIG. 7(a)) formed in the top surface of the peripheral wall 74 of the base part 70 in the objective lens socket 9, for example. Further, the motor holding member 130 holds the vibrating motor 140 such that the vibrating motor 140 penetrates through the motor holding member 130 in the horizontal direction (a direction parallel to the semiconductor device 11). That is, the vibrating motor 140 is held by the motor holding member 130 so as to extend its output shaft 141 in the horizontal direction.

A weight 142 is attached to the output shaft 141 of the vibrating motor 140. The weight 142 has, not a cylindrical shape, but an approximately L shape in section, and is structured to be eccentric to the output shaft 141, that is imbalanced in weight. Due to such a structure, when the output shaft 141 of the vibrating motor 140 is driven to rotate at a high speed, a vibration is caused in the motor holding member 130 holding the vibrating motor 140. That is, the weight 142 eccentric in weight to the output shaft 141 functions as an oscillator that causes a vibration.

The vibration caused in the vibration generator unit 120 is propagated through the holder main body 8 via the base part 70 of the objective lens socket 9, to be transmitted from the holder holding unit 60 of the holder main body 8 to the solid immersion lens 6. Then, the solid immersion lens 6 vibrates with respect to the holder holding unit 60. Accordingly, even when the solid immersion lens 6 is inhibited from freely moving as described above, that is to be forcibly cancelled by the vibration of the solid immersion lens 6.

Here, the vibration generator unit 120 and the structure of the lens holding unit 60 of the holder main body 8, i.e., the structure of holding the solid immersion lens 6 in a state of being free constitute vibration generating means for causing the solid immersion lens 6 held by the solid immersion lens holder 200 to vibrate.

Figure 10:
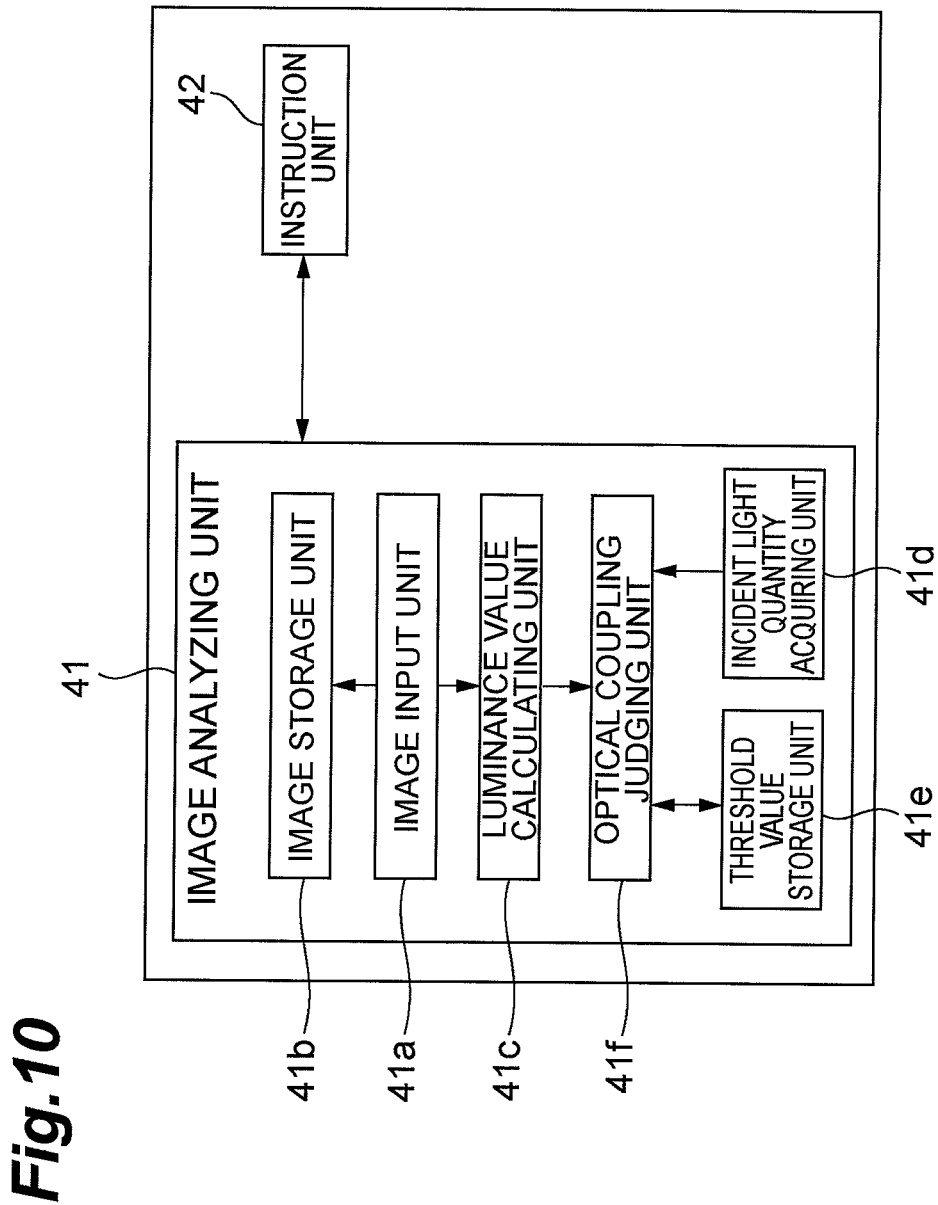
FIG. 10 is a functional block diagram of an analysis part shown in FIG. 1.

The vibrating motor 140 of the vibration generator unit 120 is controlled by an instruction from the analysis part C via the peripheral controller 33. FIG. 10 is a diagram showing a functional block of the analysis part C. In FIG. 10, the image analyzing unit 41 of the analysis part C has an image input unit 41a, an image storage unit 41b, a luminance value calculating unit 41c, an incident light quantity acquiring unit 41d, a threshold value storage unit 41e, and an optical coupling judging unit 41f.

The image input unit 41a inputs an observed image such as an emission image of the semiconductor device 11 acquired by the high-sensitivity camera 3, via the camera controller 31. Further, the image input unit 41a inputs an image of reflected light (reflected light image) of the circuit pattern from the semiconductor device 11 acquired by the LSM unit 4 or a reflected light image from the solid immersion lens 6, via the LSM controller 32. The image storage unit 41b stores these observed images and reflected light images input by the image input unit 41a.

The luminance value calculating unit 41c calculates a luminance value of a reflected light image input by the image input unit 41a, to calculate a reflected light quantity m of the reflected light image. The incident light quantity acquiring unit 41d acquires a light quantity (incident light quantity) n of an infrared laser light radiated from the LSM unit 4 to be made to come into the semiconductor device 11, from the LSM controller 32.

A reflected light image used for calculating a reflected light quantity m may be a reflected light image from the solid immersion lens 6, or may be a reflected light image from the semiconductor device 11. Hereinafter, an embodiment in which a reflected light quantity m of a reflected light image from the solid immersion lens 6 is used for a judgment of optical coupling will be described in detail.

The optical coupling judging unit 41f judges whether optical coupling (evanescent coupling) between the solid immersion lens 6 and the semiconductor device 11 is achieved on the basis of the incident light quantity n acquired by the incident light quantity acquiring unit 41d and the reflected light quantity m calculated by the luminance value calculating unit 41c. Whether evanescent coupling between the solid immersion lens 6 and the semiconductor device 11 is achieved, is judged on the basis of a reflected light quantity acquired when an infrared, laser light (incident light) radiated from the LSM unit 4 is focused on the bottom surface 6b of the solid immersion lens 6.

In detail, when an incident light is focused on the bottom surface 6b of the solid immersion lens 6 in a state in which evanescent coupling between the solid immersion lens 6 and the semiconductor device 11 is not achieved, the incident light is totally reflected by the bottom surface 6b of the solid immersion lens 6, which makes the incident light quantity and the reflected light quantity substantially equal to each other. When an incident light is focused on the bottom surface 6b of the solid immersion lens 6 in a state in which evanescent coupling is achieved on a part of the contact surface between the solid immersion lens 6 and the semiconductor device 11, only a part of the incident light is reflected by the bottom surface 6b of the solid immersion lens 6, which makes the reflected light quantity less than the incident light quantity. When an incident light is focused on the bottom surface 6b of the solid immersion lens 6 in a state in which evanescent coupling is achieved on the entire contact surface between the solid immersion lens 6 and the semiconductor device 11, most of the incident light is allowed to transmit through the semiconductor device 11, which hardly generates reflected light from the bottom surface 6b of the solid immersion lens 6.

Then, the optical coupling judging unit 41f calculates a relative ratio (m/n) between the incident light quantity n acquired by the incident light quantity acquiring unit 41d and the reflected light quantity m acquired by the luminance value calculating unit 41c, and compares a threshold value for judgment A stored in advance in the threshold value storage unit 41e with the relative ratio (m/n), to judge whether evanescent coupling between the solid immersion lens 6 and the semiconductor device 11 is achieved.

Figure 11:
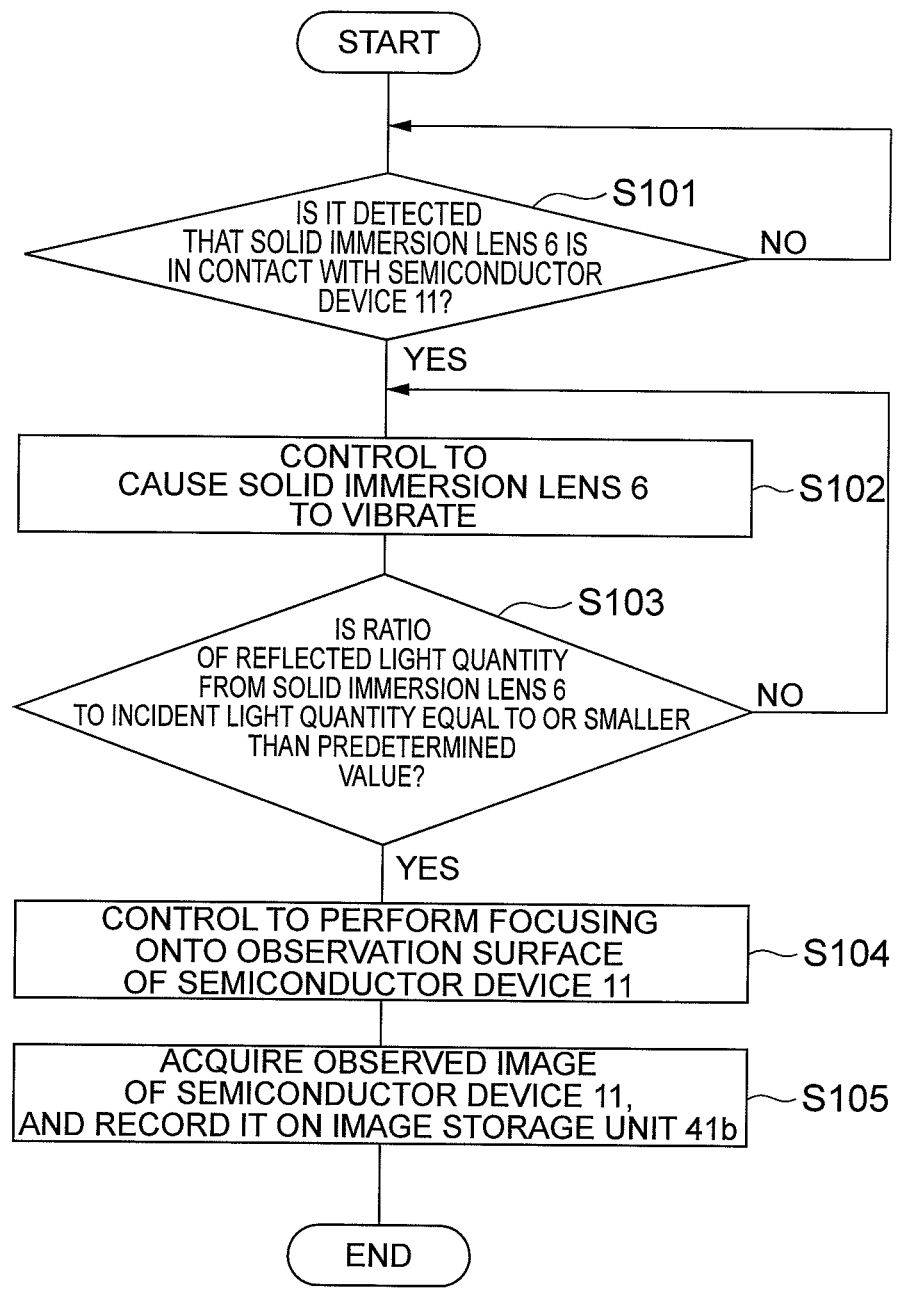
FIG. 11 is a flowchart showing details of processing steps to be executed by the analysis part when acquiring an observed image of a semiconductor device.

FIG. 11 is a flowchart showing details of processing steps to be executed by the analysis part C when acquiring an observed image of the semiconductor device 11. Hereinafter, a method for observing the semiconductor device 11 will be described with reference to the flowchart shown in FIG. 11.

First, the XYZ stage 7 is controlled to move the objective lens 21 along the optical axis L direction (the Z-axis direction) to the semiconductor device 11 side, to push down the objective lens socket 9 to the semiconductor device 11 side. Then, it is detected and judged whether the solid immersion lens 6 is in contact with the semiconductor device 11 on the basis of a detected value of the member position detecting unit 110 input via the LSM unit 4 and the peripheral controller 33 (step S101).

When it is judged that the solid immersion lens 6 is in contact with the semiconductor device 11, the driving motor 140 is driven by a control signal from the peripheral controller 33, to cause a vibration in the vibration generator unit 120 (step S102). Then, the vibration caused in the vibration generator unit 120 is transmitted to the solid immersion lens 6 via the solid immersion lens holder 200, and the solid immersion lens 6 vibrates in a state of being in contact with the semiconductor device 11.

Next, an infrared laser light (incident light) radiated from the LSM unit 4 is focused on the bottom surface 6*b* of the solid immersion lens 6, and a reflected light image from the bottom surface 6*b* of the solid immersion lens 6 is input via the LSM unit 4 and the peripheral controller 33. Then, a reflected light quantity m of the reflected light image from the bottom surface 6*b* of the solid immersion lens 6 is calculated as described above, and it is judged whether a ratio (m/n) of the reflected light quantity m to the incident light quantity n is greater than the threshold value for judgment A (step S103).

When it is judged that the ratio (m/n) of the reflected light quantity m to the incident light quantity n is greater than the threshold value for judgment A, it is judged that evanescent coupling between the solid immersion lens 6 and the semiconductor device 11 is not achieved, and the processing returns to step S102, and a vibration is again caused in the solid immersion lens holder 200 by the vibration generator unit 120, to cause the solid immersion lens 6 to vibrate.

On the other hand, when the ratio (m/n) of the reflected light quantity m to the incident light quantity n is not greater than the threshold value for judgment A, it is judged that evanescent coupling between the solid immersion lens 6 and the semiconductor device 11 is achieved, and the XYZ stage 7 is driven by a control signal from the peripheral controller 33, to perform focusing of the incident light onto a predetermined observation surface in the semiconductor device 11 (step S104). Then, an observed image of the semiconductor device 11 imaged and acquired by the high-sensitivity camera 3 is acquired from the camera controller 31, and the observed image is stored in the image storage unit 41*b* (step S105). The observation processing for the semiconductor device 11 is completed as described above.

Here, the above-described steps S101, S102, and S104 are performed in the instruction unit 42. The above-described step S103 is performed in the image input unit 41*a*, the luminance value calculating unit 41*c*, the incident light quantity acquiring unit 41*d*, the threshold value storage unit 41*e*, and the optical coupling judging unit 41*f* of the image analyzing unit 41. The above-described step S105 is performed in the image input unit 41*a* and the image storage unit 41*b* of the image analyzing unit 41.

Further, the peripheral controller 33 and the instruction unit 42 (step S102 in FIG. 11) constitute vibration control means for controlling the vibration generating means 120 to cause the solid immersion lens 6 to vibrate. The member position detecting unit 110, the LSM unit 4, the LSM controller 32, and the instruction unit 42 (step S101 in FIG. 11) constitute contact detecting means for detecting contact of the solid immersion lens 6 with the observation object 11. The LSM unit 4, the LSM controller 32, and the image input unit 41*a* of the image analyzing unit 41 constitute image acquiring means for acquiring a reflected light image from the solid immersion lens 6 or the observation object 11 when the observation object 11 is irradiated with a light by the illuminating means 4. The luminance value calculating unit 41*c*, the incident light quantity acquiring unit 41*d*, the threshold value storage unit 41*e*, and the optical coupling judging unit 41*f* of the image analyzing unit 41 constitute analysis means for analyzing a reflected light image acquired by the image acquiring means.

Next, the case in which a reflected light image from the semiconductor device 11 is used as a reflected light quantity m for a judgment of a degree of optical close contact between the solid immersion lens 6 and the semiconductor device 11 will be described.

In the above-described embodiment using a reflected light image from the bottom surface 6*b* of the solid immersion lens 6, a light is focused on the bottom surface 6*b* of the solid immersion lens 6 when acquiring a reflected light image, however, in the case in which a reflected light image from the semiconductor device 11 is used, a reflected light image acquired when a light is focused on a predetermined observation surface of the semiconductor device 11 is used. Then, the optical coupling judging unit 41*f* judges whether optical coupling (evanescent coupling) between the solid immersion lens 6 and the semiconductor device 11 is achieved on the basis of the incident light quantity n acquired by the incident light quantity acquiring unit 41*d* and the reflected light quantity m calculated by the luminance value calculating unit 41*c*.

In detail, in the same way as in the above-described embodiment, the optical coupling judging unit 41*f* calculates a relative ratio (m/n) between the incident light quantity n acquired by the incident light quantity acquiring unit 41*d* and the reflected light quantity m acquired by the luminance value calculating unit 41*c*, and compares a threshold value for judgment B stored in advance in the threshold value storage unit 41*e* with the relative ratio (m/n), to judge whether evanescent coupling between the solid immersion lens 6 and the semiconductor device 11 is achieved.

When the ratio (m/n) of the reflected light quantity m to the incident light quantity n is not greater than the threshold value for judgment B, it is judged that evanescent coupling between the solid immersion lens 6 and the semiconductor device 11 is not achieved, and the processing returns to step S102, and a vibration is again caused in the solid immersion lens holder 200 by the vibration generator unit 120, to cause the solid immersion lens 6 to vibrate.

On the other hand, when the ratio (m/n) of the reflected light quantity m to the incident light quantity n is greater than the threshold value for judgment B, it is judged that evanescent coupling between the solid immersion lens 6 and the semiconductor device 11 is achieved, and the XYZ stage 7 is driven by a control signal from the peripheral controller 33, to perform focusing of the incident light onto a predetermined observation surface in the semiconductor device 11 (step S104). Then, an observed image of the semiconductor device 11 imaged and acquired by the high-sensitivity camera 3 is acquired from the camera controller 31, and the observed image is stored in the image storage unit 41*b* (step S105). The observation processing for the semiconductor device 11 is completed as described above.

As described above, in the present embodiment, because the vibration generator unit 120 that causes the solid immersion lens holder 200 to vibrate is provided, it is possible to cause the solid immersion lens 6 to contact closely with the semiconductor device 11 while causing the solid immersion lens 6 to vibrate. Thereby, because it is prevented that the solid immersion lens 6 is inhibited from freely moving, and the bottom surface 6*b* of the solid immersion lens 6 is caused to adhere tightly along the rear surface of the semiconductor device 11, it is possible to cause the solid immersion lens 6 and the semiconductor device 11 to fully contact closely with one another. As a result, because optical evanescent coupling between the solid immersion lens 6 and the semiconductor device 11 is securely achieved, it is possible to perform a high-accuracy observation of the semiconductor device 11.

Further, because the processing for causing the solid immersion lens holder 200 to vibrate by the vibration generator unit 120 is automatically carried out until favorable optical coupling (evanescent coupling) between the solid immersion lens 6 and the semiconductor device 11 is achieved, it is possible to improve the convenience of an operator.

The preferred embodiment of the present invention has been described above, however, the present invention is not limited to the above-described embodiment.

Figure 12:
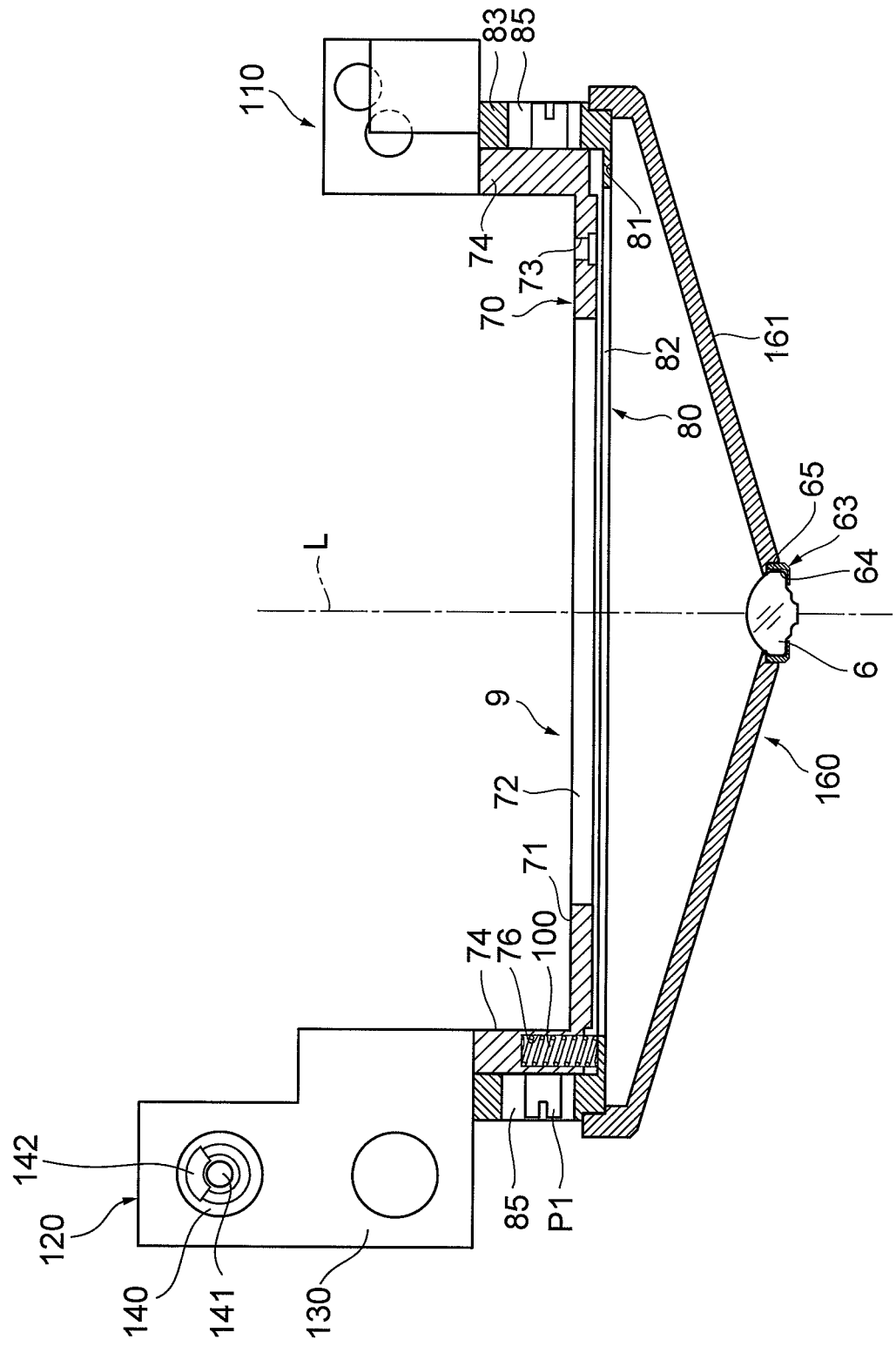
FIG. 12 is a cross sectional view showing another solid immersion lens holder as a modification.
Figure 13:
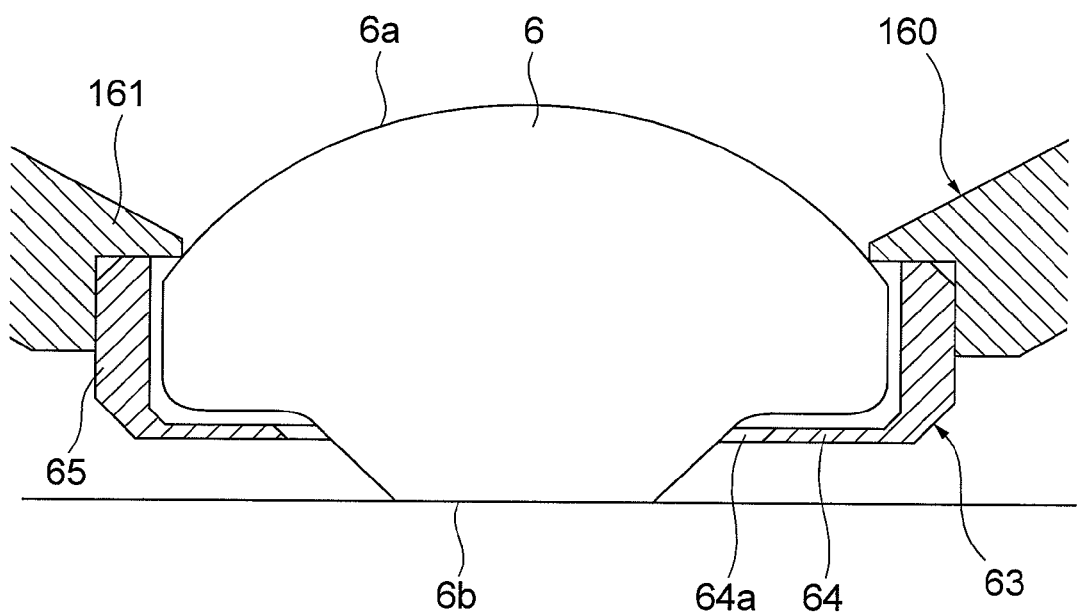
FIG. 13 is an enlarged sectional view showing a state in which the solid immersion lens is held by a lens holding member shown in FIG. 12.

For example, in the above-described embodiment, the outer shape of the holder main body 8 is formed into an approximately T-shape, however, for example, a holder main body 160 as shown in FIG. 12 may be used. The holder main body 160 has a lens holding member 161 in a tapered shape whose outer diameter becomes wider as it goes from the solid immersion lens 6 as the top to the objective lens 21 side, and the above-described lens cover 63. In this case as well, the solid immersion lens 6 is held in a state of being free with respect to the lens holding member 161 so as to project the bottom surface 6b from the opening 64a of the lens cover 63 as shown in FIG. 13.

Further, the above-described embodiment is configured such that the solid immersion lens holder 200 is attached to the front end of the objective lens 21, however, the present invention is not limited to this configuration. As another modification, there is a solid immersion lens holder configured such that the solid immersion lens 6 can be disposed between the objective lens 21 and an observation object (on the front surface side of the objective lens 21), and on the optical axis of the objective lens 21. In this case, the solid immersion lens holder is supported so as to be allowed to be inserted and removed by a manipulator, for example, and the vibration generator unit is attached to the solid immersion lens holder or the manipulator.

Figure 14:
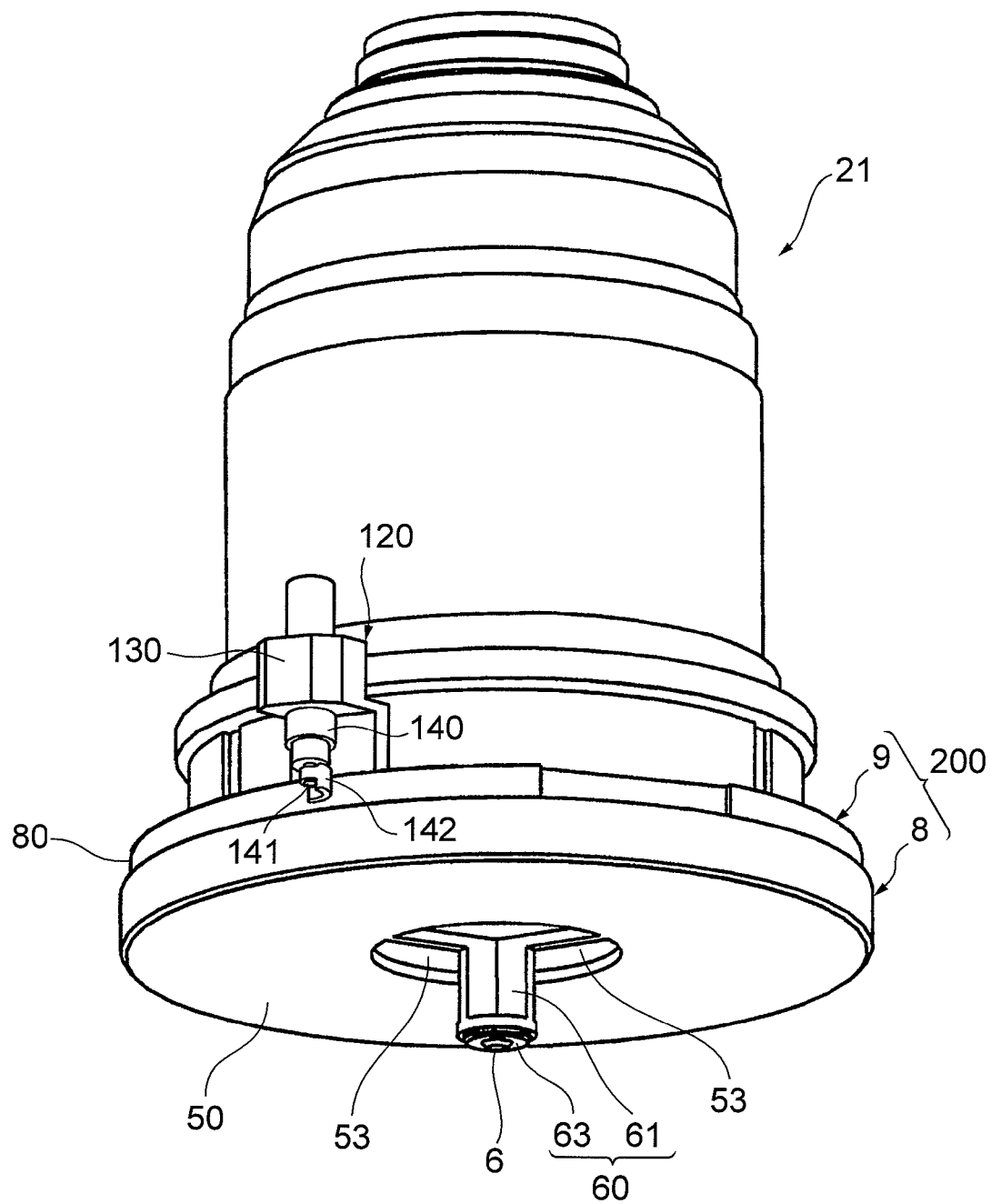
FIG. 14 is a perspective view showing yet another solid immersion lens holder along with an objective lens as a modification.

Further, in the present embodiment, the vibrating motor 140 is held such that the output shaft 141 extends in the horizontal direction by the motor holding member 130, however, as shown in FIG. 14, this may be structured such that the output shaft 141 of the vibrating motor 140 extends in the vertical direction.

Moreover, in the present embodiment, the vibration generator unit 120 is attached to the objective lens socket 9 of the solid immersion lens holder 200, however, the vibration generator unit 120 may be attached to the holder main body 8, the objective lens body tube 26 of the objective lens 21, or the like when possible.

Further, in the present embodiment, the solid immersion lens 6 is caused to vibrate under the automatic control of the vibrating motor 140, however, an observation method of the semiconductor device 11 is not particularly limited to such a fully-automatic system, and when an observer judges that favorable optical contact between the solid immersion lens 6 and the semiconductor device 11 is not achieved, the observer himself/herself may turn the vibrating motor 140 ON/OFF by manual operation.

Moreover, in the present embodiment, an observed image of the semiconductor device 11 is acquired to perform an inspection, however, it is a matter of course that a sample other than a semiconductor may be used as an observation object.

Here, the observation apparatus according to the above-described embodiment has a configuration including a microscope having an optical system including an objective lens, that magnifies an observation object to observe it, a solid immersion lens holder that holds a solid immersion lens disposed on an optical axis of the objective lens, and vibration generating means for causing the solid immersion lens held by the solid immersion lens holder to vibrate.

Further, an observation method according to the above-described embodiment has a configuration including a step of preparing an observation apparatus which includes a microscope having an optical system including an objective lens, that magnifies an observation object to observe it, a solid immersion lens holder that holds a solid immersion lens disposed on an optical axis of the objective lens, and vibration generating means for causing the solid immersion lens held by the solid immersion lens holder to vibrate, a step of causing the solid immersion lens held by the solid immersion lens holder to vibrate by the vibration generating means, and causing the solid immersion lens to contact closely with the observation object, and a step of observing the observation object with the microscope after the solid immersion lens is caused to contact closely with the observation object.

The observation apparatus described above preferably further includes vibration control means for controlling the vibration generating means to cause the solid immersion lens to vibrate. In this case, it is possible to automatically carry out the processing for causing the solid immersion lens to vibrate by the vibration generating means. Accordingly, it is possible to greatly reduce a burden on an observer.

At this time, the observation apparatus preferably further includes contact detecting means for detecting contact of the solid immersion lens with the observation object, and the vibration control means controls the vibration generating means to cause the solid immersion lens to vibrate when contact of the solid immersion lens with the observation object is detected by the contact detecting means. In this case, when the solid immersion lens comes into contact with the observation object, the solid immersion lens automatically vibrates.

Further, the observation apparatus may further include illuminating means for irradiating the observation object with light, image acquiring means for acquiring a reflected light image from the solid immersion lens or the observation object when the observation object is irradiated with a light by the illuminating means, and analysis means for analyzing the reflected light image acquired by the image acquiring means, and the vibration control means may control the vibration generating means to cause the solid immersion lens to vibrate in accordance with an analysis result of the reflected light image by the analysis means.

It is possible to judge whether the solid immersion lens and the observation object are caused to optically contact closely with one another on the basis of a reflected light image from the solid immersion lens or the observation object acquired when a light is irradiated toward the observation object. Accordingly, it is possible to easily detect the optical close contact between the solid immersion lens and the observation object by analyzing a reflected light image from the solid immersion lens or the observation object. At this time, when it is analyzed that the optical close contact between the solid immersion lens and the observation object is not favorable, the solid immersion lens is caused to automatically vibrate.

At this time, it is preferable that the analysis means has means for acquiring an incident light quantity of a light irradiated by the illuminating means, and means for comparing a ratio of a reflected light quantity of the reflected light image to the incident light quantity with a predetermined value, and the vibration control means controls the vibration generating means to cause the solid immersion lens to vibrate in accordance with a comparison result of the ratio of the reflected light quantity to the incident light quantity with the predetermined value.

A ratio between a reflected light quantity of a reflected light image from the solid immersion lens or the observation object and an incident light quantity to the observation object differs depending on a state of optical coupling (evanescent coupling) between the solid immersion lens and the observation object. For example, the higher the ratio of a reflected light quantity of a reflected light image from the solid immersion lens to an incident light quantity becomes, the more difficult it is to achieve optical coupling between the solid immersion lens and the observation object. Accordingly, provided that the solid immersion lens is caused to vibrate when a ratio of a reflected light quantity from the solid immersion lens to an incident light quantity is greater than a predetermined value, it is possible to more securely achieve the favorable close contact between the solid immersion lens and the observation object.

INDUSTRIAL APPLICABILITY

The present invention is available for an observation apparatus and method capable of improving the close contact between the solid immersion lens and an observation object.

The invention claimed is:

1. An observation apparatus comprising:
   a microscope having an optical system including an objective lens, the microscope magnifies an observation object to observe it;
   a solid immersion lens holder that holds a solid immersion lens disposed on an optical axis of the objective lens;
   vibration generator configured to cause the solid immersion lens held by the solid immersion lens holder to vibrate; and
   vibration controller configured to control the vibration generator to cause the solid immersion lens to vibrate, wherein
   the solid immersion lens holder includes a lens holding unit that holds the solid immersion lens in a state of being unfixed to be free, and
   the vibration generator is configured to cause the solid immersion lens to vibrate so that the solid immersion lens vibrates with respect to the lens holding unit.

2. The observation apparatus according to claim 1, further comprising a contact detector configured to detect contact of the solid immersion lens with the observation object, wherein
   the vibration controller controls the vibration generator to cause the solid immersion lens to vibrate when contact of the solid immersion lens with the observation object is detected by the contact detector.

3. The observation apparatus according to claim 1, further comprising:
   illuminator configured to irradiate the observation object with light;
   image acquiring arrangement configured to acquire a reflected light image from the solid immersion lens or the observation object when the observation object is irradiated with the light by the illuminator; and
   analysis portion configured to analyze the reflected light image acquired by the image acquiring arrangement, wherein
   the vibration controller controls the vibration generator to cause the solid immersion lens to vibrate in accordance with an analysis result of the reflected light image by the analysis portion.

4. The observation apparatus according to claim 3, wherein
   the analysis portion has an arrangement for acquiring an incident light quantity of the light irradiated by the illuminator, and a portion configured to compare a ratio of a reflected light quantity of the reflected light image to the incident light quantity with a predetermined value, and
   the vibration controller controls the vibration generator to cause the solid immersion lens to vibrate in accordance with a comparison result of the ratio of the reflected light quantity to the incident light quantity with the predetermined value.

5. The observation apparatus according to claim 1, wherein the vibration generator includes a vibrating motor disposed so as to extend its output shaft in a direction parallel to the observation object.

6. The observation apparatus according to claim 1, wherein the vibration generator includes a vibrating motor disposed so as to extend its output shaft in a direction vertical to the observation object.

7. An observation method comprising:
   a step of preparing an observation apparatus which includes a microscope having an optical system including an objective lens, that magnifies an observation object to observe it, a solid immersion lens holder that holds a solid immersion lens disposed on an optical axis of the objective lens and includes a lens holding unit that holds the solid immersion lens in a state of being unfixed to be free, and vibration generator configured to cause the solid immersion lens held by the solid immersion lens holder to vibrate;
   a step of causing the solid immersion lens held by the solid immersion lens holder to vibrate by the vibration generator so that the solid immersion lens vibrates with respect to the lens holding unit, and causing the solid immersion lens to contact closely with the observation object; and
   a step of observing the observation object with the microscope after the solid immersion lens is caused to contact closely with the observation object.

8. The observation method according to claim 7, wherein the vibration generator includes a vibrating motor disposed so as to extend its output shaft in a direction parallel to the observation object.

9. The observation method according to claim 7, wherein the vibration generator includes a vibrating motor disposed so as to extend its output shaft in a direction vertical to the observation object.

* * * * *

UNITED STATES PATENT AND TRADEMARK OFFICE
CERTIFICATE OF CORRECTION

PATENT NO. : 8,582,202 B2  
APPLICATION NO. : 12/665588  
DATED : November 12, 2013  
INVENTOR(S) : Terada et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 839 days.

Signed and Sealed this
Twenty-second Day of September, 2015

Michelle K. Lee
*Director of the United States Patent and Trademark Office*